United States Patent
Wang

(10) Patent No.: US 9,374,880 B2
(45) Date of Patent: Jun. 21, 2016

(54) METHOD AND APPARATUS FOR MODULATING CURRENT IN COMPUTED TOMOGRAPHY IMAGING SYSTEM

(71) Applicant: Shenyang Neusoft Medical Systems Co., Ltd., Shenyang (CN)

(72) Inventor: Hongbo Wang, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 221 days.

(21) Appl. No.: 14/142,956

(22) Filed: Dec. 30, 2013

(65) Prior Publication Data
US 2015/0003593 A1 Jan. 1, 2015

(30) Foreign Application Priority Data
Jun. 26, 2013 (CN) .......................... 2013 1 0261627

(51) Int. Cl.
*H05G 1/34* (2006.01)
*H05G 1/10* (2006.01)
(Continued)

(52) U.S. Cl.
CPC *H05G 1/34* (2013.01); *A61B 6/405* (2013.01); *A61B 6/54* (2013.01); *H05G 1/265* (2013.01); *G05B 2219/33155* (2013.01);
(Continued)

(58) Field of Classification Search
CPC .......... H05G 1/00; H05G 1/08; H05G 1/085; H05G 1/10; H05G 1/26; H05G 1/265; H05G 1/30; H05G 1/34; H05G 1/60; A61B 6/00; A61B 6/40; A61B 6/405; A61B 6/54; A61B 6/56; H03C 1/00; H03C 1/02; H03C 1/08; H03C 1/10; G05B 19/234; G05B 19/255; G05B 19/295; G05B 19/315; G05B 19/355; G05B 19/375; G05B 2219/33155; G05B 2219/36495; G05B 2219/41043; G05B 2219/41051; G05B 2219/41214; G05B 2219/41383; G05B 2219/42067
See application file for complete search history.

(56) References Cited

U.S. PATENT DOCUMENTS

2005/0185759 A1 8/2005 Toth et al.
2010/0254509 A1* 10/2010 Sugaya .................. A61B 6/032
378/16

FOREIGN PATENT DOCUMENTS

CN 1657008 A 8/2005

OTHER PUBLICATIONS

C. Amara et al., Approxmation of the Curves by B-Spline, published on Mathematical Theory and Applications, vol. 22 No. 1, Jun. 2002, 3 pages.

(Continued)

*Primary Examiner* — Anastasia Midkiff
(74) *Attorney, Agent, or Firm* — Kilpatrick Townsend & Stockton LLP

(57) ABSTRACT

A method and apparatus of current modulation in a computed tomography imaging system are provided. The method may include: selecting a plurality of sample points from an expected current modulation curve as approach points; establishing an actual current modulation curve, wherein an actual current value of the actual current modulation curve at an approach point approximates an expected current value of an expected current modulation curve, and a variation rate of the actual current is within an allowed range of the computed tomography imaging system; and modulating a current in an X-ray tube of the computed tomography imaging system according to the actual current modulation curve. According to the disclosure, an image valuable to the diagnosis can be obtained with the smallest radiation dose.

14 Claims, 6 Drawing Sheets

(51) Int. Cl.
*A61B 6/00* (2006.01)
*H05G 1/08* (2006.01)
*H03C 1/10* (2006.01)
*H05G 1/26* (2006.01)

(52) U.S. Cl.
CPC ............. *G05B 2219/36495* (2013.01); *G05B 2219/41214* (2013.01); *G05B 2219/42067* (2013.01); *H03C 1/10* (2013.01); *H05G 1/08* (2013.01); *H05G 1/10* (2013.01)

(56) References Cited

OTHER PUBLICATIONS

Dong Wang et al., B-spline Curve Fitting Using Equality-constrained Least Squares, published on Acta Scientiarum Naturalium Universitatis Sunyatseni, vol. 47 No. 4, Jul. 2008, 4 pages.

\* cited by examiner

METHOD AND APPARATUS FOR MODULATING CURRENT IN COMPUTED TOMOGRAPHY IMAGING SYSTEM

CROSS REFERENCE TO RELATED APPLICATIONS

The present application claims priority to Chinese patent application No. 201310261627.8, filed on Jun. 26, 2013, and entitled "Method and Apparatus for Modulating Current in Computed Tomography Imaging System", the entire disclosure of which is incorporated herein by reference.

TECHNICAL FIELD

The present disclosure generally relates to medical imaging technology, and more particularly, to a method and apparatus for modulating current in a computed tomography imaging system.

BACKGROUND

In Computed Tomography (CT) imaging system, an accurate and collimating X-ray source and a high-sensitivity detector are employed for a series of tomographic scanning around a part of a human body. In the process of scanning, the X-ray beam attenuates when passing through the human body and the attenuated X-ray beam is received by the detector. Then, an analog value is converted into a digital value and input into a computer. The computer may obtain a value of an X-ray absorption coefficient of every point in a cross-section by high-speed calculation. The data of all the values of all the points may constitute an image matrix. Thereafter, the data may be shown with different gray levels through a display. As such, an anatomical structure of the cross-section can be clearly shown through a monitor. Alternately, a multiformat camera or a laser camera may be used to record the image on a photograph.

The X-ray source typically includes an X-ray tube which can emit X-ray under the drive of a tube current. When the X-ray tube is driven by a relatively large current, a clear image may be obtained. However, the human body is in turn exposed under a large radiation (namely, large radiation dose). Otherwise, when the X-ray tube is driven by a relatively small current, a serious image distortion may occur although the human body is exposed under a small radiation (namely, small radiation dose). Therefore, it is desired to obtain an image valuable to the diagnosis with the smallest radiation dose.

Currently, an ideal current modulation curve can be determined based on current modulation technology. Referring to FIG. 1, on the ideal current modulation curve, different expected current values can be determined according to different scanning angle. An image valuable to the diagnosis may be obtained with the X-ray tube driven under the determined expected current value with a smallest radiation dose.

However, referring to FIG. 1, it is found that there exists at least following issues in the current technology, an actual current value can not reach the determined expected current value due to an inherent limitation of the computed tomography imaging system, which in turn result in an image not valuable to the diagnosis with the smallest radiation dose.

SUMMARY

Embodiments of the present disclosure provide a method and apparatus for modulating current in a computed tomography imaging system, which literally achieves an image valuable to the diagnosis with the smallest radiation dose.

In one embodiment, a current modulation method in a computed tomography imaging system is provided, which may include:

selecting a plurality of discrete data points from an expected current modulation curve as approach points;

establishing an actual current modulation curve, wherein an actual current value of the actual current modulation curve at an approach point approximates an expected current value of an expected current modulation curve, and a variation rate of the actual current is within an allowed range of the computed tomography imaging system; and modulating a current in an X-ray tube of the computed tomography imaging system according to the actual current modulation curve.

In some embodiments, before establishing an actual current modulation curve, the method may further include:

setting an approach factor for an actual current at an approach point, where the greater the approach factor, the higher the approaching degree, and the smaller the approach factor, the lower the approaching degree, wherein after setting an approach factor for an actual current at an approach point, the method further includes:

establishing an actual current modulation curve, wherein an actual current value of the actual current modulation curve at an approach point approximates an expected current value of an expected current modulation curve according to the set approach factor, and a variation rate of the actual current is within an allowed range of the computed tomography imaging system.

In some embodiments, setting an approach factor for an actual current at an approach point may include:

selecting from the approach points a plurality of peak points and/or valley points of the expected current modulation curve;

sorting the peak points and/or valley points in an ascending order of amplitudes, and setting approach factors in an incremental way for actual currents at the sorted peak points and/or valley points; and setting approach factors equal to 1 for actual currents at the approach points not including the peak points and/or valley points.

In some embodiments, before sorting the peak points and/or valley points in an ascending order of amplitudes, and setting approach factors in an incremental way for actual currents at the sorted peak points and/or valley points, the method may further include:

filtering out some peak points and/or valley points not satisfying a predetermined condition from the selected peak points and/or valley points, the remaining peak points and/or valley points satisfying the predetermined condition;

wherein after filtering, the method further comprises:

sorting the remaining peak points and/or valley points in an ascending order of amplitudes, and setting approach factors in an incremental way for actual currents at the sorted peak points and/or valley points; and setting approach factors equal to 1 for actual currents at the approach points not including the peak points and/or valley points which do not satisfy the predetermined condition.

In some embodiments, setting approach factors in an incremental way for actual currents at the sorted peak points and/or valley points may include:

calculating a summation of all expected current values at positions of the sorted peak points and/or valley points of an expected current modulation curve; and calculating a product of a serial number and the summation, wherein the product equals to an approach factor of an actual current value at a position of the sorted peak points and/or valley points.

In some embodiments, the step of establishing an actual current modulation curve, wherein an actual current value of the actual current modulation curve at an approach point approximates an expected current value of an expected current modulation curve, and a variation rate of the actual current is within an allowed range of the computed tomography imaging system, includes"

calculating an actual current value, where the actual current value satisfies the requirements: the norm of a difference between the actual current value and an expected current value of an expected current modulation curve at an approach point is minimum; and a variation rate of the actual current is within an allowed range of the computed tomography imaging system; and determining an actual current modulation curve according to the actual current value.

In some embodiments, the step of establishing an actual current modulation curve, wherein an actual current value of the actual current modulation curve at an approach point approximates an expected current value of an expected current modulation curve according to the set approach factor, and a variation rate of the actual current is within an allowed range of the computed tomography imaging system, may include:

calculating an actual current value, where the actual current value satisfies the requirements: a product of the set approach factor and the norm of a difference between the actual current value and an expected current value of an expected current modulation curve at an approach point is minimum; and a variation rate of the actual current is within an allowed range of the computed tomography imaging system; and determining an actual current modulation curve according to the actual current value.

In one embodiment, a current modulation apparatus in a computed tomography imaging system is provided, which may include:

an approach point selecting device, configured to select a plurality of sample points from an expected current modulation curve as approach points;

an actual current modulation curve establishing device, configured to establish an actual current modulation curve, wherein an actual current value of the actual current modulation curve at an approach point approximates an expected current value of an expected current modulation curve, and a variation rate of the actual current is within an allowed range of the computed tomography imaging system; and a current modulation device, configured to modulate a current in an X-ray tube of the computed tomography imaging system according to the actual current modulation curve.

In some embodiments, the apparatus may further include:

a approach factor setting module, configured to set an approach factor for an actual current at an approach point before the actual current modulation curve establishing device establishes an actual current modulation curve, where the greater the approach factor, the higher the approaching degree, and the smaller the approach factor, the lower the approaching degree, wherein the actual current modulation curve establishing device is configured to establish an actual current modulation curve, wherein an actual current value of the actual current modulation curve at an approach point approximates an expected current value of an expected current modulation curve according to the set approach factor, and a variation rate of the actual current is within an allowed range of the computed tomography imaging system.

In some embodiments, the approach factor setting module may include:

a selection sub-module, configured to select from the approach points a plurality of peak points and/or valley points of the expected current modulation curve;

a first setting sub-module, configured to sort the peak points and/or valley points in an ascending order of amplitudes, and set approach factors in an incremental way for actual currents at the sorted peak points and/or valley points; and a second setting sub-module, configured to set approach factors equal to 1 for actual currents at the approach points not including the peak points and/or valley points.

In some embodiments, the approach factor setting module may further include:

a filtering sub-module, configured to filter out some peak points and/or valley points not satisfying a predetermined condition from the peak points and/or valley points selected by the selection sub-module, the remaining peak points and/or valley points satisfying the predetermined condition, wherein the first setting sub-module is configured to sort the remaining peak points and/or valley points in an ascending order of amplitudes, and set approach factors in an incremental way for actual currents at the sorted peak points and/or valley points, and the second setting sub-module is configured to set approach factors equal to 1 for actual currents at the approach points not including the peak points and/or valley points which do not satisfy the predetermined condition.

In some embodiments, the first setting sub-module may include:

a summation calculation sub-module, configured to calculate a summation of all expected current values at positions of the sorted peak points and/or valley points of an expected current modulation curve; and a product calculation sub-module, configured to calculate a product of a serial number and the summation, wherein the product equals to an approach factor of an actual current value at a position of the sorted peak points and/or valley points.

In some embodiments, the actual current modulation curve establishing device may include:

a first actual current value calculation sub-module, configured to calculate an actual current value, where the actual current value satisfies the requirements: the norm of a difference between the actual current value and an expected current value of an expected current modulation curve at an approach point is minimum; and a variation rate of the actual current is within an allowed range of the computed tomography imaging system; and a first actual current modulation curve determination sub-module, configured to determine an actual current modulation curve according to the actual current value.

In some embodiments, the actual current modulation curve establishing device may include:

a second actual current value calculation sub-module, configured to calculate an actual current value, where the actual current value satisfies the requirements: a product of the set approach factor and the norm of a difference between the actual current value and an expected current value of an expected current modulation curve at an approach point is minimum; and a variation rate of the actual current is within an allowed range of the computed tomography imaging system; and a second actual current modulation curve determination sub-module, configured to determine an actual current modulation curve according to the actual current value.

Embodiments of the present disclosure have the following advantages:

The requirements for a current variation rate are taken into full consideration in the computed tomography imaging system. An actual current at an approach point approximates an expected current value of an expected current modulation curve, and a variation rate of the actual current is within an allowed range of the computed tomography imaging system. In this way, an image valuable to the diagnosis can be generated with the smallest radiation dose.

In addition, by setting an approach factor, it is achievable that approaching degrees between actual current values and expected current values at different approach points are different, which is thus suitable for various scenarios.

BRIEF DESCRIPTION OF THE DRAWINGS

A further understanding of the nature and advantages of various embodiments may be realized by reference to the following figures. The accompanying drawings are presented for descriptive purpose, but not intended to be limiting. To those skilled in the art, other accompanying drawings may be obtained according to the disclosure without creative work.

DETAILED DESCRIPTION

In order to clarify the objects, characteristics and advantages of the disclosure, the embodiments of the present disclosure will be described in detail in conjunction with the accompanying drawings.

Embodiment One

Figure 1:
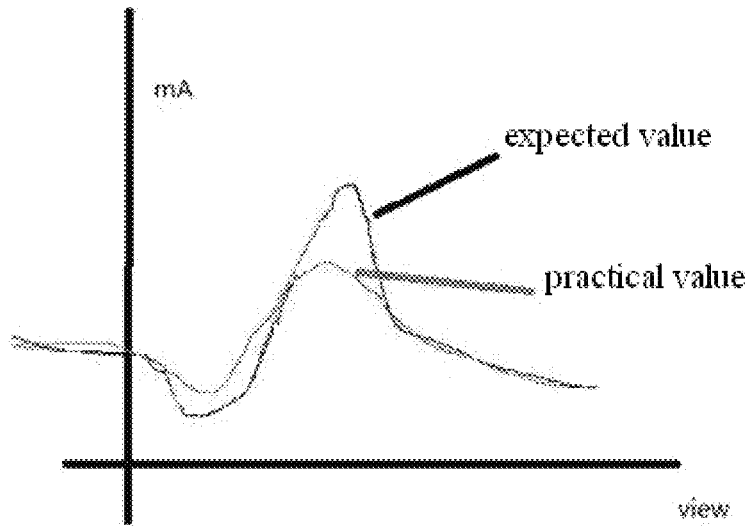
FIG. 1 illustrates schematic views of an ideal current modulation curve and an actual current modulation curve according to current method.
Figure 2:
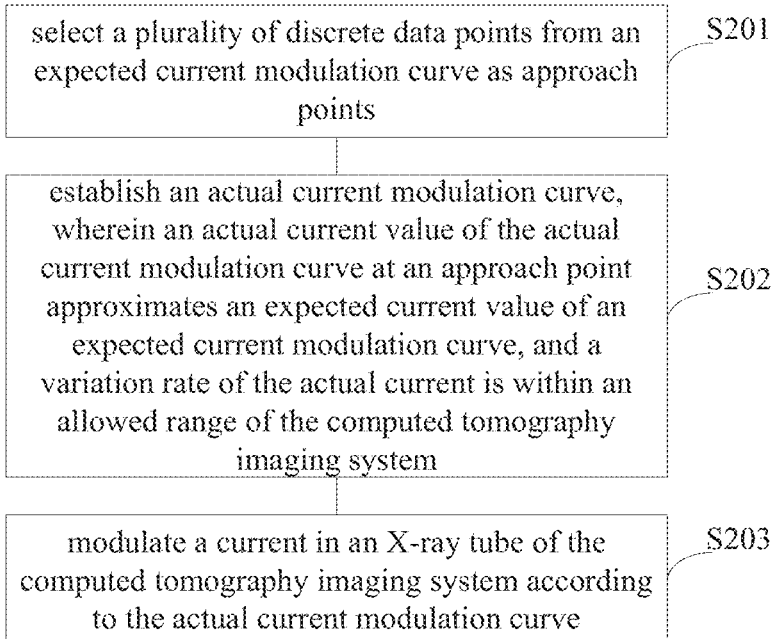
FIG. 2 schematically illustrates a flow chart of a current modulation method in a computed tomography imaging system according to a first embodiment of the present disclosure.

Referring to FIG. 2, FIG. 2 schematically illustrates a flow chart of a current modulation method in a computed tomography imaging system according to the first embodiment of the present disclosure. The current modulation method may include steps of S201, S202 and S203.

S201, select a plurality of discrete data points from an expected current modulation curve as approach points;

The term "expected current modulation curve", as used herein, is intended to refer to a current modulation curve under ideal conditions which may be obtained by any one of conventional methods. The expected current modulation curve is actually composed of a group of discrete data points. Each of the discrete data points may be selected as an approach point. Alternatively, some of the discrete data points may be selected as approach points. For example, assuming that the expected current modulation curve is composed of 1000 discrete data points, 500 data points may be selected out of the 1000 discrete data points as approach points. A curve g(t) has an expected current value $d_i$ at positions of the 500 approach points, where $i=1, \ldots N$, and $N=500$.

It should be noted that, the number of the approach points does not tend to limit the scope of present disclosure. Of course, the greater the number of the approach points, the closer the actual current modulation curve approximates the ideal current modulation curve.

S202, establish an actual current modulation curve, wherein an actual current value of the actual current modulation curve at an approach point approximates an expected current value of an expected current modulation curve, and a variation rate of the actual current is within an allowed range of the computed tomography imaging system;

Assuming that the actual current value of the actual current modulation curve at positions of (n+1) approach points equals to $x_i$, where $i=0, \ldots n$, $x_i$ should meet the following conditions:

1, the value of $x_i$ needs to approximate $d_i$;

2, considering the requirements for the current variation rate in a CT system, the smallest current variation rate allowed by the system is $b_0$, and the greatest current variation rate allowed by the system is $b_1$. That is, the range of current variation rate allowed by the system is $[b_0, b_1]$. Therefore, $x_i - x_{i-1}$ (where $i=1, \ldots n$) should be within the range of current variation rate allowed by the system, namely, $b_0 < x_i - x_{i-1} < b_1$.

In order to make the value of $x_i$ approximate $d_i$, a mathematical model $\|x_i - d_i\|$ may be established, where $\|.\|$ represents norm calculation. When $\|x_i - d_i\|$ approach to the smallest value, the value of $x_i$ approximates $d_i$. For example, when $\|.\|$ is used for 1-norm calculation, it is equivalent to calculate an absolute value. When $\|.\|$ is used for 2-norm calculation, it is equivalent to calculate the square root of the mean of the squared pixel values.

Hereunder, a mathematical method for calculating an actual current value is provided, which satisfies the following two requirements: the norm of a difference between an actual current value and an expected current value of an expected current modulation curve at an approach point is minimum; and a variation rate of the actual current is within an allowed range of the computed tomography imaging system.

1. establish a mathematical model satisfying the first requirement:

$$\min\left(\sum_{i=1}^{n} \|x_i - d_i\|\right),$$

where the operator min( ) represents for calculating the minimum value.

The object function may be transformed to obtain equation (1):

$$\min(\|X-D\|) \qquad \text{equation (1)}$$

where X or D is a column vector, and components in D represent expected current values selected from the expected current modulation curve, $$D = \begin{pmatrix} d_1 \\ d_2 \\ \vdots \\ d_n \end{pmatrix}_{n \times 1}$$

2. establish a mathematical model satisfying the second requirement:

$$\begin{cases} b_0 < x_1 - x_0 < b_1 \\ b_0 < x_2 - x_1 < b_1 \\ \vdots \\ b_0 < x_n - x_{n-1} < b_1 \end{cases}$$

Let $t_i = x_i - x_{i-1}$, $i = 1, \ldots n$, then $$\begin{cases} t_1 = x_1 - x_0 \\ t_2 = x_2 - x_1 \\ \vdots \\ t_n = x_n - x_{n-1} \end{cases}$$

after a transformation, then $$\begin{cases} x_1 = x_0 + t_1 \\ x_2 = x_0 + t_1 + t_2 \\ \vdots \\ x_n = x_0 + t_1 + t_2 + \ldots + t_n \end{cases}$$

Therefore, equation (2) can be obtained:

$$X = A \times T + X_0 \qquad \text{equation (2)}$$

where A represents a lower triangular matrix, T represents a column vector. $X_0$ represents a column vector, and $x_0$ represents a given initial current value, wherein $$A = \begin{bmatrix} 1 & \cdots & 0 \\ \vdots & \ddots & \vdots \\ 1 & \cdots & 1 \end{bmatrix}_{n \times n}, T = \begin{pmatrix} t_1 \\ t_2 \\ \vdots \\ t_n \end{pmatrix}_{n \times 1}, \text{ and } X_0 = \begin{pmatrix} x_0 \\ x_0 \\ \vdots \\ x_0 \end{pmatrix}_{n \times 1}$$

If the equation (2) is taken into the equation (1), $\min(\|A \times T + X_0 - D\|)$ is obtained, where $b_0 \le T \le b_1$. T satisfying the conditions may be calculated by numeric calculation. Then X can be further obtained based on T, where components in X are actual current values which satisfy the requirements: the norm of a difference between an actual current value and an expected current value of an expected current modulation curve at an approach point is minimum; and a variation rate of the actual current is within an allowed range of the computed tomography imaging system. Afterwards, an actual current curve can be determined according to the obtained actual current values. Based on the actual current curve, different actual current values can be determined corresponding to different scanning angle.

S203, modulate a current in an X-ray tube of the computed tomography imaging system according to the actual current modulation curve.

According to a scanning angle and an actual current value corresponding to the scanning angle of the actual current modulation curve, the current in the X-ray tube of the computed tomography imaging system can be modulated.

In light of the first embodiment, the present disclosure has the following advantages:

The requirements for a current variation rate are taken into full consideration in the computed tomography imaging system. An actual current at an approach point approximates an expected current value of an expected current modulation curve, and a variation rate of the actual current is within an allowed range of the computed tomography imaging system. In this way, an image valuable to the diagnosis can be generated with the smallest radiation dose.

Embodiment Two

In some special situations, it needs to know whether or not an actual current value in an X-ray tube reaches a predetermined expected current value at a specific approach point (namely, a specific position). For example, in order to obtain a good-quality image, it needs to know whether or not an actual current value at a peak point reaches an expected current value. For another example, in order to decrease scanning dose and avoid damages to human body, it needs to know whether or not an actual current value at a valley point reaches an expected current value.

Figure 3:
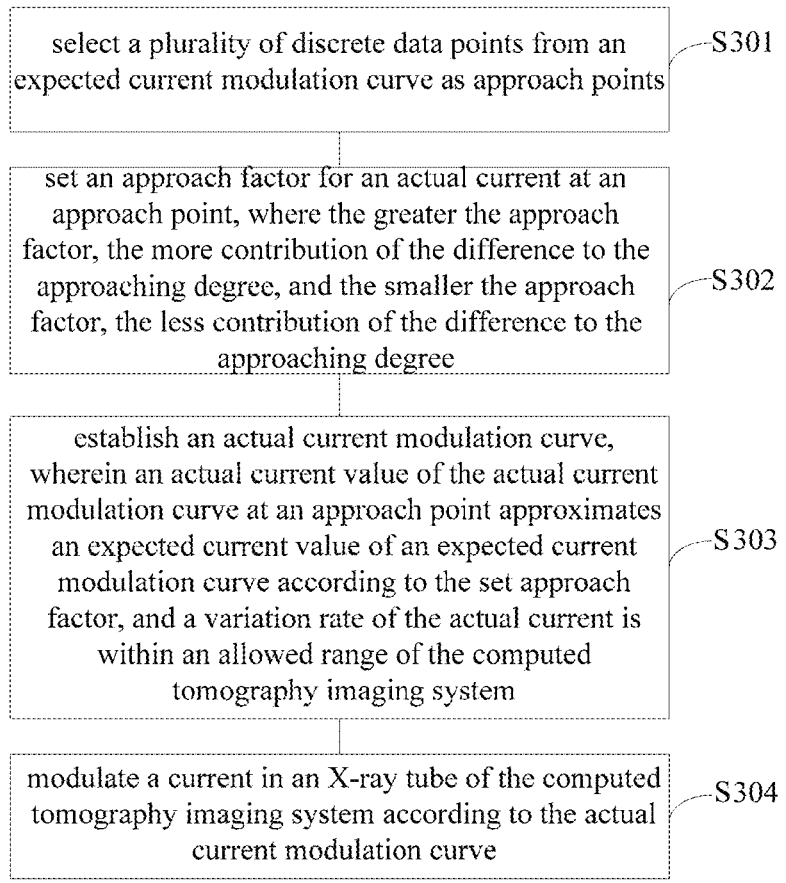
FIG. 3 schematically illustrates a flow chart of a current modulation method in a computed tomography imaging system according to a second embodiment of the present disclosure.

Compared with the first embodiment, an approach factor is set for an actual current value in the second embodiment. The degree of approximation between an actual current value and an expected current value changes with the approach factor. Referring to FIG. 3, FIG. 3 schematically illustrates a flow chart of a current modulation method in a computed tomography imaging system according to the second embodiment of the present disclosure. The method includes the steps of S301 to S304.

S301, select a plurality of discrete data points from an expected current modulation curve as approach points;

More information about selecting approach points may refer to S201 in the first embodiment, and will not be described in detail herein.

S302, set an approach factor for an actual current at an approach point, where the greater the approach factor, the more contribution of the difference to the approaching degree, and the smaller the approach factor, the less contribution of the difference to the approaching degree.

In practical application, different approach factors can be set for actual current values at different approach points according to practical requirements. The greater the approach factor at an approach point, the higher a degree of approximation between an actual current value and an expected current value at the approach point. Whereas, the less the approach factor at an approach point, the lower a degree of approximation between an actual current value and an expected current value at the approach point. In some embodiments, a same approach factor can be set for all actual current values at different approach points. That is, the degrees of approximation between all actual current values and expected current values at different approach points are the same.

For example, in order to obtain a good-quality image, the degree of approximation between an actual current value and an expected current value at a peak point should be relatively high, while the degree of approximation between an actual current value and an expected current value at a position other than the peak point should be relatively low. Therefore, for all approach points, a relatively great approach factor may be set for an actual current value at the peak point, and a relative small approach factor may be set for an actual current value at a position other than the peak point.

For actual current values at all peak points, a same approach factor or different approach factors may be set. In some embodiments, different approach factors may be set depending on the amplitude of a peak point. For example, all the peak points may be sorted in an ascending order of amplitudes. Then, approach factors may be set in an incremental way for actual current values at the sorted peak points. As such, a relatively great approach factor can be guaranteed for an actual current value at a peak point with a large amplitude, while a relatively small approach factor can be guaranteed for an actual current value at a peak point with a small amplitude. As a result, an image with good quality may be obtained and the problem that it is difficult to reach an expected current value in the process of current modulation due to an inherent limitation of the computed tomography imaging system can be avoided.

For another example, in order to decrease scanning dose and avoid damages to human body, the degree of approximation between an actual current value and an expected current value at a valley point should be relatively high, while the degree of approximation between an actual current value and an expected current value at a position other than the valley point should be relatively low. Therefore, for all approach points, a relatively great approach factor can be set for an actual current value at the valley point, and a relative small approach factor can be set for an actual current value at a position other than the valley point.

For actual current values at all valley points, a same approach factor or different approach factors may be set. In some embodiments, different approach factors may be set depending on the amplitude of a valley point. For example, all the valley points may be sorted in an ascending order of amplitudes. Then, approach factors may be set in an incremental way for actual currents at the sorted valley points. As such, a relatively great approach factor can be guaranteed for an actual current value at a valley point with a large amplitude, while a relatively small approach factor can be guaranteed for an actual current value at a valley point with a small amplitude. As a result, an image with good quality may be obtained and the problem that it is difficult to reach an expected current value in the process of current modulation due to an inherent limitation of the computed tomography imaging system can be avoided.

In some embodiments, if considering both a good-quality image and a scanning dose, approach factors for an actual current value at a peak point and for an actual current value at a valley point may be set according to the above methods, respectively.

In some embodiments, assuming that approach factors need to be set for actual current values at positions of m peak points or m valley points, an equation for setting an approach factor may be $$w_i = i \times \sum_{i=1}^{m} g_i,$$

where $w_i$ represents an approach factor, m represents the number of the peak points or valley points, i represents the serial number in an ascending order, and $g_i$ represents an expected current value at a peak point or a valley point. From the equation, the smaller the serial number i (namely, the peak point or valley point has a small amplitude), the smaller the approach factor, while the greater the s serial number i (namely, the peak point or valley point has a large amplitude), the greater the approach factor. Approach factors of actual current values at positions other than the peak points and valley points equal to 1.

S303, establish an actual current modulation curve, wherein an actual current value of the actual current modulation curve at an approach point approximates an expected current value of an expected current modulation curve according to the set approach factor, and a variation rate of the actual current is within an allowed range of the computed tomography imaging system;

Below, a mathematical method for calculating an actual current value is provided when an approach factor is set for an actual current.

A mathematical model satisfying the first requirement is established, which is $$\min\left(\sum_{i=1}^{n} \|x_i - d_i\| w_i\right),$$

where the operator min( ) represents for calculating the minimum value.

The object function may be transformed as following:

$$\min(W^T \times \|X - D\|) \qquad \text{equation (3)}$$

where W, X or D is a column vector, components in D represent expected current values selected from the expected current modulation curve, and components in W represent approach factors of the actual current at all approach points, $$D = \begin{pmatrix} d_1 \\ d_2 \\ \vdots \\ d_n \end{pmatrix}_{n \times 1}, W = \begin{pmatrix} w_1 \\ w_2 \\ \vdots \\ w_n \end{pmatrix}_{n \times 1}$$

Taking the equation (2) into the equation (3), $\min(W^T \times \|A \times T + X_0 - D\|)$ is obtained, where $b_0 \leq T \leq b_1$. T satisfying the conditions may be calculated by numeric calculation. Then X can be further obtained based on T, where components in X are actual current values which satisfy the requirements: a product of the set approach factor and the norm of a difference between an actual current value and an expected current value of an expected current modulation curve at an approach point is minimum; and a variation rate of the actual current is within an allowed range of the computed tomography imaging system. Afterwards, an actual current curve can be determined according to the obtained actual current values. Based on the actual current curve, different actual current values can be determined corresponding to different scanning angle.

S304, modulate a current in an X-ray tube of the computed tomography imaging system according to the actual current modulation curve.

In light of the second embodiment, the present disclosure has the following advantages compared with the prior art:

The requirements for a current variation rate are taken into full consideration in the computed tomography imaging system. An actual current at an approach point approximates an expected current value of an expected current modulation curve, and a variation rate of the actual current is within an allowed range of the computed tomography imaging system. In this way, an image valuable to the diagnosis can be generated with the smallest radiation dose.

In addition, by setting an approach factor, it is achievable that degrees of approximation between actual current values and expected current values at different approach points are different, which is thus suitable for various scenarios.

Embodiment Three

Compared with the second embodiment, in the third embodiment, when setting an approach factor for an actual current at a peak point, some peak points which do not satisfy a predetermined condition are filtered out after peak points are selected, so as to reduce the amount of work for setting approach factors. Likewise, similar processes may be applied to valley points.

Figure 4:
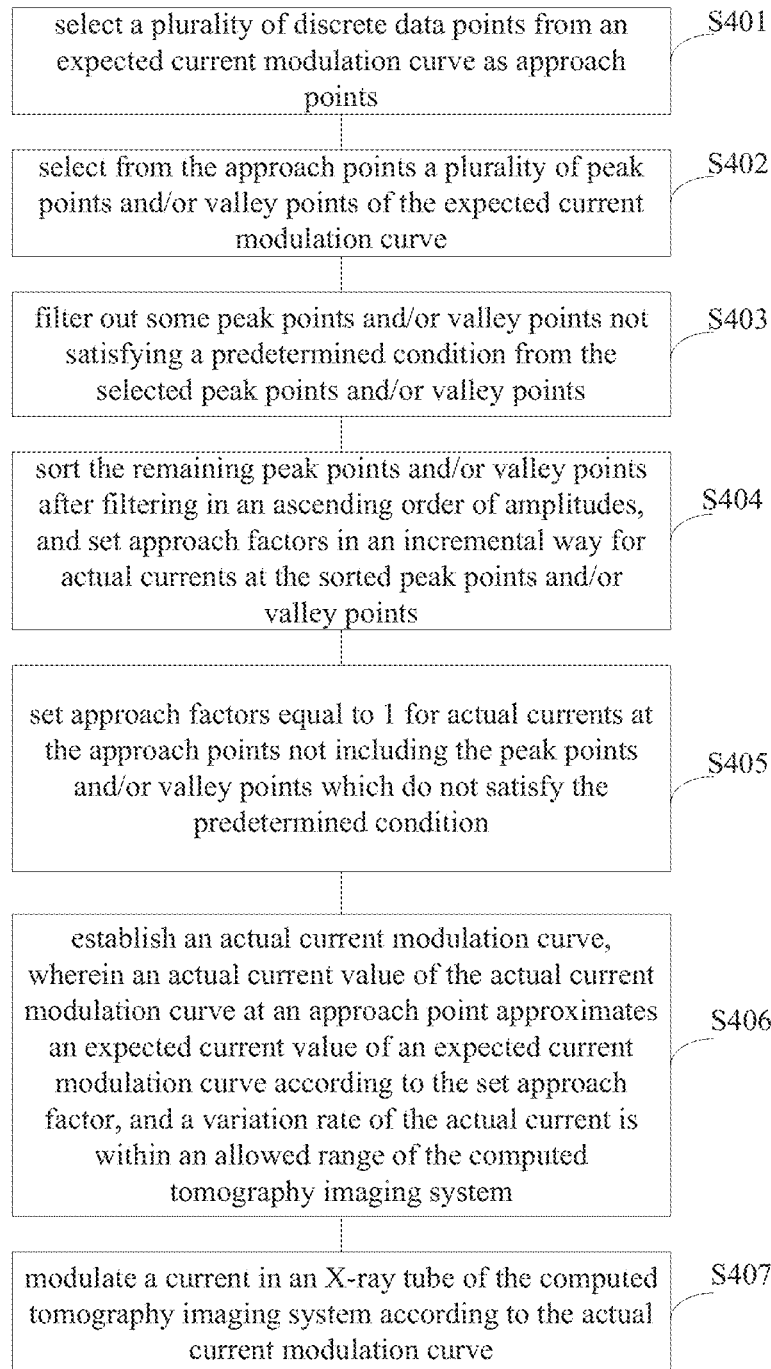
FIG. 4 schematically illustrates a flow chart of a current modulation method in a computed tomography imaging system according to a third embodiment of the present disclosure.

Referring to FIG. 4, FIG. 4 schematically illustrates a flow chart of a current modulation method in a computed tomography imaging system according to the third embodiment of the present disclosure. The method includes the steps of S401 to S407.

S401, select a plurality of discrete data points from an expected current modulation curve as approach points;

S402, select from the approach points a plurality of peak points and/or valley points of the expected current modulation curve;

S403, filter out some peak points and/or valley points not satisfying a predetermined condition from the selected peak points and/or valley points, the remaining peak points and/or valley points satisfying the predetermined condition acting as candidate points;

For example, the predetermined condition may be that an expected current value at a peak point or a valley point is greater than a predetermined current threshold, or an interval between two neighboring peak points or two neighboring valley points is greater than a predetermined interval threshold.

S404, sort the remaining peak points and/or valley points after filtering (i.e., the candidate points) in an ascending order of amplitudes, and set approach factors in an incremental way for actual currents at the sorted peak points and/or valley points;

S405, set approach factors equal to 1 for actual currents at the approach points not including the peak points and/or valley points which do not satisfy the predetermined condition;

S406, establish an actual current modulation curve, wherein an actual current value of the actual current modulation curve at an approach point approximates an expected current value of an expected current modulation curve according to the set approach factor, and a variation rate of the actual current is within an allowed range of the computed tomography imaging system;

S407, modulate a current in an X-ray tube of the computed tomography imaging system according to the actual current modulation curve.

Other than S403, the steps in the third embodiment may refer to the second embodiment respectively, and will not be described in detail herein.

In light of the second embodiment, the present disclosure has the following advantages compared with the prior art:

The requirements for a current variation rate are taken into full consideration in the computed tomography imaging system. An actual current at an approach point approximates an expected current value of an expected current modulation curve, and a variation rate of the actual current is within an allowed range of the computed tomography imaging system. In this way, an image valuable to the diagnosis can be generated with the smallest radiation dose.

In addition, by setting an approach factor, it is achievable that degrees of approximation between actual current values and expected current values at different approach points are different, which is thus suitable for various scenarios.

Embodiment Four

Figure 5:
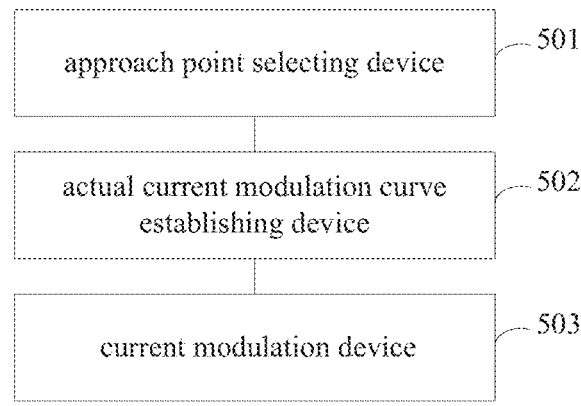
FIG. 5 schematically illustrates a structural view of a current modulation apparatus in a computed tomography imaging system according to a fourth embodiment of the present disclosure.

Corresponding to a current modulation method in a computed tomography imaging system described above, a current modulation apparatus in a computed tomography imaging system is also provided. Referring to FIG. 5, FIG. 5 schematically illustrates a structural view of a current modulation apparatus in a computed tomography imaging system according to a fourth embodiment of the present disclosure. The current modulation apparatus includes an approach point selecting device 501, an actual current modulation curve establishing device 502, and a current modulation device 503. Hereinafter, an internal structure and a connection relationship of the apparatus will be described in detail accompanying with its operation principle.

The approach point selecting device 501 is configured to select a plurality of sample points from an expected current modulation curve as approach points.

The actual current modulation curve establishing device 502 is configured to establish an actual current modulation curve, wherein an actual current value of the actual current modulation curve at an approach point approximates an expected current value of an expected current modulation curve, and a variation rate of the actual current is within an allowed range of the computed tomography imaging system.

The current modulation device 503 is configured to modulate a current in an X-ray tube of the computed tomography imaging system according to the actual current modulation curve.

Figure 6:
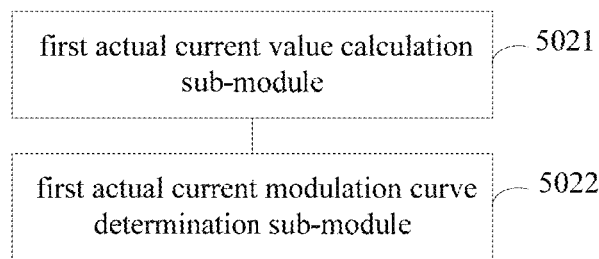
FIG. 6 schematically illustrates a structural view of a device for establishing an actual current modulation curve according to one embodiment of the present disclosure.

In some embodiments, referring to FIG. 6, the actual current modulation curve establishing device 502 includes a first actual current value calculation sub-module 5021 and a first actual current modulation curve determination sub-module 5022.

The first actual current value calculation sub-module 5021 is configured to calculate an actual current value, where the actual current value satisfies the requirements: the norm of a difference between the actual current value and an expected current value of an expected current modulation curve at an approach point is minimum; and a variation rate of the actual current is within an allowed range of the computed tomography imaging system.

The first actual current modulation curve determination sub-module 5022 is configured to determine an actual current modulation curve according to the actual current value.

Figure 7:
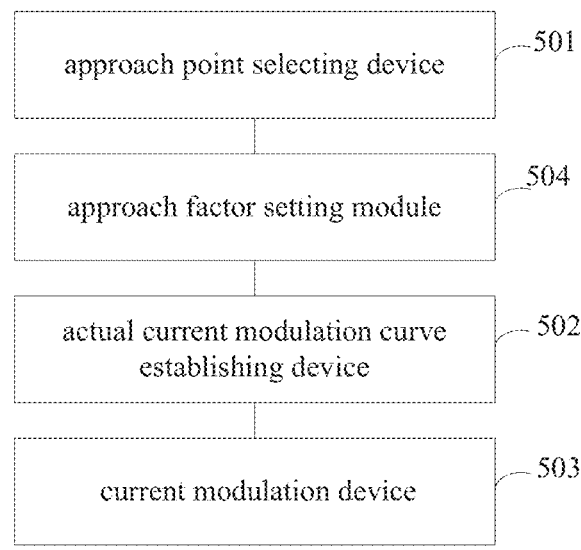
FIG. 7 schematically illustrates another structural view of a current modulation apparatus in a computed tomography imaging system according to the fourth embodiment of the present disclosure.

Referring to FIG. 7, the apparatus may further include an approach factor setting module 504. The approach factor setting module 504 is configured to set an approach factor for an actual current at an approach point before the actual current modulation curve establishing device 502 establishes an actual current modulation curve, where the greater the approach factor, the more contribution of the difference to the approaching degree, and the smaller the approach factor, the less contribution of the difference to the approaching degree.

The actual current modulation curve establishing device 502 is configured to establish an actual current modulation curve, wherein an actual current value of the actual current modulation curve at an approach point approximates an expected current value of an expected current modulation curve according to the set approach factor, and a variation rate of the actual current is within an allowed range of the computed tomography imaging system.

In some embodiments, the actual current modulation curve establishing device 502 shown in FIG. 7 may further include a second actual current value calculation sub-module and a second actual current modulation curve determination sub-module. The second actual current value calculation sub-module is configured to calculate an actual current value, where the actual current value satisfies the requirements: a product of the set approach factor and the norm of a difference between the actual current value and an expected current value of an expected current modulation curve at an approach point is minimum; and a variation rate of the actual current is within an allowed range of the computed tomography imaging system. The second actual current modulation curve determination sub-module is configured to determine an actual current modulation curve according to the actual current value.

Figure 8:
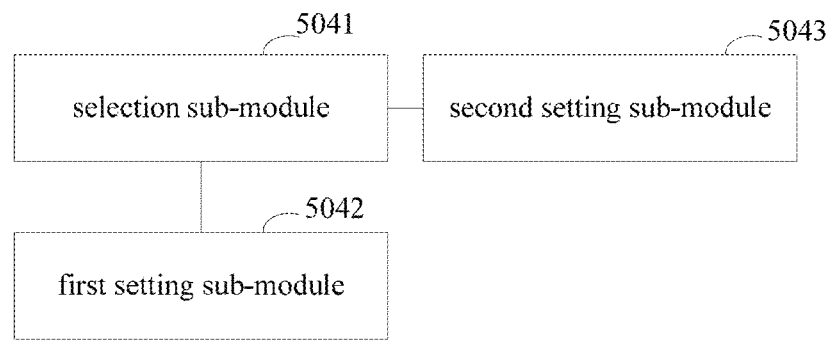
FIG. 8 schematically illustrates a structural view of a device for setting an approach factor according to one embodiment of the present disclosure.

In some embodiments, referring to FIG. 8, the approach factor setting module 504 may further include a selection sub-module 5041, a first setting sub-module 5042 and a second setting sub-module 5043.

The selection sub-module 5041 is configured to select from the approach points a plurality of peak points and/or valley points of the expected current modulation curve.

The first setting sub-module 5042 is configured to sort the peak points and/or valley points in an ascending order of amplitudes, and set approach factors in an incremental way for actual currents at positions of the sorted peak points and/or valley points.

The second setting sub-module 5043 is configured to set approach factors equal to 1 for actual currents at the approach points not including the peak points and/or valley points.

Figure 9:
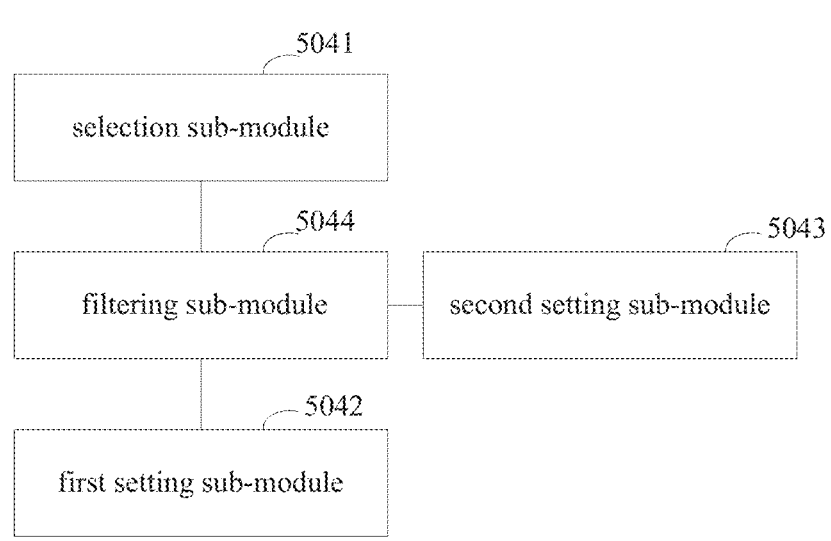
FIG. 9 schematically illustrates another structural view of a approach factor setting module according to one embodiment of the present disclosure.

Other than the structure shown in FIG. 8, the approach factor setting module 504 may further include a filtering sub-module 5044 shown in FIG. 9, which is configured to filter out some peak points and/or valley points not satisfying a predetermined condition from the peak points and/or valley points selected by the selection sub-module.

The first setting sub-module 5042 is configured to sort the peak points and/or valley points, from which some peak points and/or valley points not satisfying the predetermined condition have been filtered out, in an ascending order of amplitudes, and set approach factors in an incremental way for actual currents at positions of the sorted peak points and/or valley points.

The second setting sub-module 5043 is configured to set approach factors equal to 1 for actual currents at the approach points not including the peak points and/or valley points which do not satisfy the predetermined condition.

In some embodiments, the first setting sub-module may include: a summation calculation sub-module configured to calculate a summation of all expected current values at positions of the sorted peak points and/or valley points of an expected current modulation curve; and a product calculation sub-module configured to calculate a product of a serial number and the summation, wherein the product equals to an approach factor of an actual current value at a position of the sorted peak points and/or valley points.

In light of above embodiments, the embodiments of the present disclosure has the following advantages:

The requirements for a current variation rate are taken into full consideration in the computed tomography imaging system. An actual current at an approach point approximates an expected current value of an expected current modulation curve, and a variation rate of the actual current is within an allowed range of the computed tomography imaging system. In this way, an image valuable to the diagnosis can be generated with the smallest radiation dose.

In addition, by setting an approach factor, it is achievable that degrees of approximation between actual current values and expected current values at different approach points are different, which is thus suitable for various scenarios.

Figure 10:
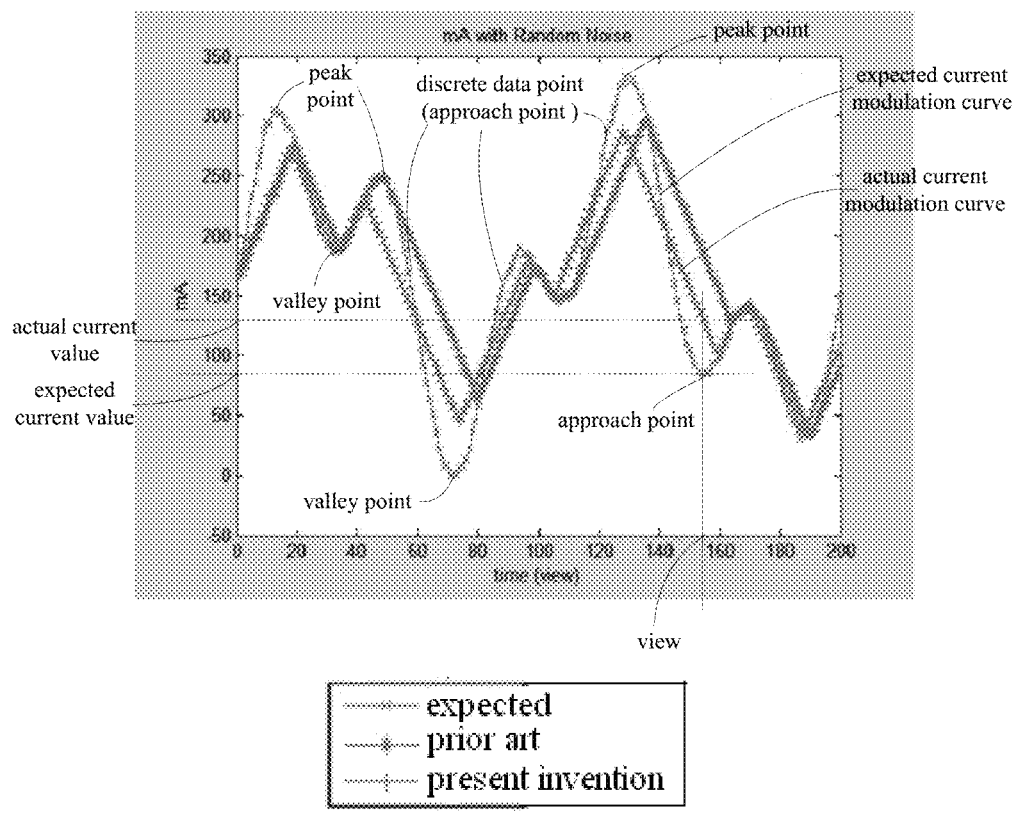
FIG. 10 schematically illustrates an experimental results according to one embodiments described above.

When the current modulation method provided in the first embodiment is simulated using matlab, the experimental results are shown in FIG. 10.

It will be apparent to those skilled in the art that some or all of the procedures of such methods provided in embodiments of the present disclosure may be performed by related hardware in response to some computer programs. The computer programs may be stored in a computer-readable storage medium, which may execute the processes of the methods described in the above embodiments. The storage medium may be an optical disk, a magnetic disk, a Read-Only Memory (ROM), or a Random Access Memory (RAM), etc.

Although the present disclosure has been disclosed above with reference to preferred embodiments thereof, it should be understood that the disclosure is presented by way of example only, and not limitation. Those skilled in the art can modify and vary the embodiments without departing from the spirit and scope of the present disclosure.

I claim:

1. A current modulation method in a computed tomography imaging system, comprising:

selecting a plurality of discrete data points from an expected current modulation curve as approach points, wherein each of the approach points represents an expected current at a view;

setting an approach factor for each actual current value, which comprises:

selecting from the approach points a plurality of peak points and/or valley points of the expected current modulation curve, sorting the peak points and/or valley points in an ascending order of amplitudes, setting the approach factors in an incremental way for the actual current values at the views corresponding to the sorted peak points and/or valley points, respectively, and setting the approach factors equal to 1 for the actual current values at the views corresponding to the approach points except the peak points and/or valley points;

establishing an actual current modulation curve, wherein at each view, the actual current value of the actual current modulation curve approximates the corresponding expected current value of the expected current modulation curve, and a variation rate of the actual current value is within an allowed range of the computed tomography imaging system, thus the actual current modulation curve has an approaching degree to the expected current modulation curve, and the approaching degree is determined by differences between the actual current values and the corresponding expected current values; and modulating a current in an X-ray tube of the computed tomography imaging system according to the actual current modulation curve.

2. The method according to claim 1,
wherein the greater the approach factor, the more contribution of the difference to the approaching degree, and the smaller the approach factor, the less contribution of the difference to the approaching degree,
wherein the approaching degree is determined by a sum of the differences that multiplied by the corresponding factors.

3. The method according to claim 1, before setting the approach factors in an incremental way for the actual current values at the views corresponding to the sorted peak points and/or valley points, the method further comprises:
filtering out some of the peak points and/or valley points not satisfying a predetermined condition from the sorted peak points and/or valley points, wherein remaining peak points and/or valley points satisfies the predetermined condition;
wherein after filtering, the method further comprises:
sorting the remaining peak points and/or valley points in the ascending order of amplitudes, and setting the approach factors in the incremental way for the actual current values at the views corresponding to the remaining peak points and/or valley points; and
setting the approach factors equal to 1 for the actual current values at the views corresponding to the approach points except the remaining peak points and/or valley points.

4. The method according to claim 1, wherein setting the approach factors in an incremental way for the actual current values at the views corresponding to the sorted peak points and/or valley points comprises:
calculating a summation of the expected current values corresponding to the sorted peak points and/or valley points of an expected current modulation curve; and
calculating a product of a serial number of each sorted peak points and/or valley points and the summation, wherein the products equal the approach factors of the actual current values at the views corresponding to the sorted peak points and/or valley points.

5. The method according to claim 1, wherein the step of establishing an actual current modulation curve comprises:
calculating the actual current values, where each actual current value satisfies the requirements: the sum of the differences that multiplied by the corresponding factors is minimum, and a variation rate of the actual current is within an allowed range of the computed tomography imaging system; and
determining the actual current modulation curve according to the actual current value.

6. The method according to claim 1, wherein setting the approach factors in an incremental way for the actual current values at the views corresponding to the sorted peak points and/or valley points comprises:
calculating a summation of the expected current values at the views corresponding to the sorted peak points and/or valley points of the expected current modulation curve; and
calculating a product of a serial number of each sorted peak points and/or valley points and the summation, wherein the products equal the approach factors of the actual current values at the views corresponding to the sorted peak points and/or valley points, respectively.

7. A current modulation apparatus in a computed tomography imaging system, comprising:
an approach point selecting device, configured to select a plurality of discrete data points from an expected current modulation curve as approach points, wherein each of the approach points represents an expected current at a view;
an approach factor setting module, configured to set an approach factor for each actual current, which comprises:
a selection sub-module, configured to select from the approach points a plurality of peak points and/or valley points of the expected current modulation curve, a first setting sub-module, configured to sort the peak points and/or valley points in an ascending order of amplitudes, and set the approach factors in an incremental way for actual current values at the views corresponding to the sorted peak points and/or valley points, respectively, and
a second setting sub-module, configured to set the approach factors equal to 1 for the actual current values at the views corresponding to the approach points except the peak points and/or valley points;
an actual current modulation curve establishing device, configured to establish an actual current modulation curve, wherein at each view, an actual current value of the actual current modulation curve approximates the corresponding expected current value of the expected current modulation curve, and a variation rate of the actual current is within an allowed range of the computed tomography imaging system, thus the actual current modulation curve has an approaching degree to the expected current modulation curve, and the approaching degree is determined by differences between the actual current values and the corresponding expected current values; and
a current modulation device, configured to modulate a current in an X-ray tube of the computed tomography imaging system according to the actual current modulation curve.

8. The apparatus according to claim 7, further comprising:
wherein the greater the approach factor, the more contribution of the difference to the approaching degree, and the smaller the approach factor, the less contribution of the difference to the approaching degree,
wherein the approaching degree is determined by a sum of the differences that multiplied by the corresponding factors.

9. The apparatus according to claim 7, wherein the approach factor setting module further comprises:
a filtering sub-module, configured to filter out some of the peak points and/or valley points not satisfying a predetermined condition from the peak points and/or valley points selected by the selection sub-module, wherein the remaining peak points and/or valley points satisfies the predetermined condition,
wherein the first setting sub-module is configured to sort the remaining peak points and/or valley points in the ascending order of amplitudes, and set the approach factors in the incremental way for the actual current values at the views corresponding to the sorted peak points and/or valley points, and the second setting sub-module is configured to set the approach factors equal to 1 for the actual current values at the views corresponding to the approach points except the remaining peak points and/or valley points.

10. The apparatus according to claim 7, wherein the first setting sub-module comprises:
a summation calculation sub-module, configured to calculate a summation of the expected current values corresponding to the sorted peak points and/or valley points of an expected current modulation curve; and
a product calculation sub-module, configured to calculate a product of a serial number of each sorted peak points and/or valley points and the summation, wherein the products equal the approach factors of the actual current values at the views corresponding to the sorted peak points and/or valley points.

11. The apparatus according to claim 7, wherein the actual current modulation curve establishing device comprises:
a second actual current value calculation sub-module, configured to calculate the actual current values, where each actual current value satisfies the requirements: the sum of the differences that multiplied by the corresponding factors is minimum, and a variation rate of the actual current is within an allowed range of the computed tomography imaging system; and
a second actual current modulation curve determination sub-module, configured to determine the actual current modulation curve according to the actual current value.

12. The apparatus according to claim 7, wherein the first setting sub-module comprises:
a summation calculation sub-module, configured to calculate a summation of the expected current values at of the views corresponding to the sorted peak points and/or valley points of the expected current modulation curve; and
a product calculation sub-module, configured to calculate a product of a serial number of each sorted peak points and/or valley points and the summation, wherein the products equal the approach factors of the actual current values at the views corresponding to the sorted peak points and/or valley points, respectively.

13. A current modulation method in a computed tomography imaging system, comprising:
selecting a plurality of discrete data points from an expected current modulation curve as approach points, wherein each of the approach points represents an expected current at a view;
establishing an actual current modulation curve, wherein at each view, the actual current value of the actual current modulation curve approximates the corresponding expected current value of the expected current modulation curve, and a variation rate of the actual current value is within an allowed range of the computed tomography imaging system, thus the actual current modulation curve has an approaching degree to the expected current modulation curve, and the approaching degree is determined by differences between the actual current values and the corresponding expected current values; and
modulating a current in an X-ray tube of the computed tomography imaging system according to the actual current modulation curve;
wherein the step of establishing an actual current modulation curve comprises:
calculating the actual current values, where each actual current value satisfies the requirements: a norm of the difference between the actual current value and the corresponding expected current value of the expected current modulation curve at the corresponding view is minimum, thus the approaching degree is a minimum value of a sum of the differences between the actual current values and the corresponding expected current values; and a variation rate of the actual current is within an allowed range of the computed tomography imaging system; and
determining the actual current modulation curve according to the actual current value.

14. A current modulation apparatus in a computed tomography imaging system, comprising:
an approach point selecting device, configured to select a plurality of discrete data points from an expected current modulation curve as approach points, wherein each of the approach points represents an expected current at a view;
an actual current modulation curve establishing device, configured to establish an actual current modulation curve, wherein at each view, an actual current value of the actual current modulation curve approximates the corresponding expected current value of the expected current modulation curve, and a variation rate of the actual current is within an allowed range of the computed tomography imaging system, thus the actual current modulation curve has an approaching degree to the expected current modulation curve, and the approaching degree is determined by differences between the actual current values and the corresponding expected current values; and
a current modulation device, configured to modulate a current in an X-ray tube of the computed tomography imaging system according to the actual current modulation curve;
wherein the actual current modulation curve establishing device comprises:
a first actual current value calculation sub-module, configured to calculate the actual current values, where each actual current value satisfies the requirements: a norm of the difference between the actual current value and the corresponding expected current value of the expected current modulation curve at the corresponding view is minimum, thus the approaching degree is a minimum value of a sum of the differences between the actual current values and the corresponding expected current values; and a variation rate of the actual current value is within an allowed range of the computed tomography imaging system; and
a first actual current modulation curve determination sub-module, configured to determine the actual current modulation curve according to the actual current value.

* * * * *